(12) United States Patent
Haag et al.

(10) Patent No.: US 11,458,665 B2
(45) Date of Patent: Oct. 4, 2022

(54) SINGLE-SHAFT EXTRUDER AND USE OF A SINGLE-SHAFT EXTRUDER, AND METHOD FOR ALTERING MORPHOLOGY OF A SUPERABSORBENT POLYMER GEL USING A SINGLE-SHAFT EXTRUDER

(71) Applicant: BASF SE, Ludwigshafen (DE)

(72) Inventors: Monica Haag, Ludwigshafen (DE);
Stephan Deuerlein, Ludwigshafen (DE); Holger Barthel, Ludwigshafen (DE); Volker Klock, Ludwigshafen (DE); Roland Krauss, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 331 days.

(21) Appl. No.: 16/470,590

(22) PCT Filed: Dec. 15, 2017

(86) PCT No.: PCT/EP2017/083107
§ 371 (c)(1),
(2) Date: Jun. 18, 2019

(87) PCT Pub. No.: WO2018/114703
PCT Pub. Date: Jun. 28, 2018

(65) Prior Publication Data
US 2019/0308358 A1    Oct. 10, 2019

(30) Foreign Application Priority Data

Dec. 21, 2016 (EP) .................................... 16205993

(51) Int. Cl.
*B29C 48/00* (2019.01)
*B29C 48/63* (2019.01)
(Continued)

(52) U.S. Cl.
CPC ............ *B29C 48/022* (2019.02); *B29B 7/422* (2013.01); *B29B 7/429* (2013.01); *B29C 48/397* (2019.02);
(Continued)

(58) Field of Classification Search
CPC ..... B29C 48/022; B29C 48/63; B29C 48/681; B29C 48/397; B29C 48/535; B29C 48/625; B29C 48/687
See application file for complete search history.

(56) References Cited

U.S. PATENT DOCUMENTS 4,129,386 A * 12/1978 Rauwendaal ......... B29C 48/501
366/88
4,199,263 A    4/1980 Menges et al.
(Continued)

FOREIGN PATENT DOCUMENTS

CA         1016316 A      8/1977
CN       102712712 A    10/2012
(Continued)

OTHER PUBLICATIONS

Kutz (ed.), Applied Plastics Engineering Handbook: Processing and Materials, Elsevier, Metering Mechanism pp. 237-245 (2011).
(Continued)

*Primary Examiner* — Galen H Hauth
(74) *Attorney, Agent, or Firm* — Marshall, Gerstein & Borun LLP (57) ABSTRACT

A single-screw extruder for changing a morphology of a superabsorbent polymer, specifically a polymer gel. The single-screw extruder has an input aperture, a channel, a screw and an output aperture. The screw has a pitch value of a pitch of the screw flights along the conveying zone of the channel, where the channel has a mixing-element arrangement with at least one mixing element which protrudes into the channel of the single-screw extruder and which is configured for the mixing of the SAP polymer gel.

19 Claims, 4 Drawing Sheets

(51) Int. Cl.
    *B29C 48/68*    (2019.01)
    *B29C 48/395*   (2019.01)
    *B29C 48/535*   (2019.01)
    *B29C 48/625*   (2019.01)
    *B29C 48/685*   (2019.01)
    *B29B 7/42*     (2006.01)
    *C08J 3/075*    (2006.01)
    *C08L 101/14*   (2006.01)
    *B29K 105/00*   (2006.01)

(52) U.S. Cl.
    CPC .......... *B29C 48/535* (2019.02); *B29C 48/625* (2019.02); *B29C 48/63* (2019.02); *B29C 48/681* (2019.02); *B29C 48/687* (2019.02); *C08J 3/075* (2013.01); *C08L 101/14* (2013.01); *B29K 2105/0061* (2013.01); *C08J 2333/06* (2013.01)

(56) References Cited

U.S. PATENT DOCUMENTS

| | | | |
|---|---|---|---|
| 4,720,254 A * | 1/1988 | Wood | B29C 48/687 425/208 |
| 2012/0258851 A1 | 10/2012 | Nakatsuru et al. | |
| 2016/0199529 A1 * | 7/2016 | Torii | B29B 15/00 428/402 |
| 2018/0141258 A1 * | 5/2018 | Zabel | B29C 48/395 |

FOREIGN PATENT DOCUMENTS

| | | |
|---|---|---|
| DE | 2235784 A1 | 1/1974 |
| EP | 0209328 A2 | 1/1987 |
| EP | 0490361 A1 | 6/1992 |
| EP | 0509779 A2 | 10/1992 |
| EP | 1510317 B1 | 2/2007 |
| EP | 2208756 A1 | 7/2010 |
| EP | 2557095 A1 | 2/2013 |
| JP | S57133038 A | 8/1982 |
| JP | S5859342 A | 4/1983 |
| JP | S58128832 A | 8/1983 |
| JP | H04353424 A | 12/1992 |
| JP | H1177667 A | 3/1999 |
| JP | 2001-079829 A | 3/2001 |
| JP | 2001-301006 A | 10/2001 |
| JP | 2002-177807 A | 6/2002 |
| JP | 2005-001231 A | 1/2005 |
| JP | 2005-272653 A | 10/2005 |
| JP | 2010-505003 A | 2/2010 |
| WO | WO-2014/118024 A1 | 8/2014 |

OTHER PUBLICATIONS

International Application No. PCT/EP2017/083106, International Search Report, dated Mar. 5, 2018.

* cited by examiner

SINGLE-SHAFT EXTRUDER AND USE OF A SINGLE-SHAFT EXTRUDER, AND METHOD FOR ALTERING MORPHOLOGY OF A SUPERABSORBENT POLYMER GEL USING A SINGLE-SHAFT EXTRUDER

CROSS-REFERENCE TO RELATED APPLICATIONS

This is a U.S. national phase of International Application No. PCT/EP2017/083107 filed Dec. 15, 2017, which claims the benefit of European Patent Application No. 16205993.5, filed Dec. 21, 2016.

The present invention relates to a single-screw extruder according to the preamble of claim 1 for changing a morphology of superabsorbent polymer gel (SAP polymer gel), and to the use of same, in particular for the pelletization of the superabsorbent polymer gel (SAP polymer gel), and to a process for changing a morphology of an SAP polymer gel with the single-screw extruder.

WO 2014/118024 A1 describes a process for the production of water-absorbent polymer particles with high swelling rate and high centrifuge retention capacity together with high permeability of the swollen gel bed via polymerization of an aqueous monomer solution in a polymerization reactor with at least two shafts rotating around parallel axes (kneader). A polymer gel arising therefrom is then subjected to extrusion with exposure to high temperatures and thermal surface-postcrosslinking. The temperature of the polymer gel during extrusion is above 80° C., and during extrusion less than 60 kWh/t of specific mechanical energy is introduced. The specific mechanical energy (SME) introduced during extrusion can be influenced by way of example via the ratio of internal length to internal diameter of the extruder (L/D). The specific mechanical energy (SME) is the power delivered by the extruder motor in kW divided by the throughput of polymer gel in t/h. It is advantageous to use short extruders. Excessive pressures during extrusion are thus avoided. During extrusion, the polymer gel is forced through the perforations of a perforated plate. The properties of water-absorbent polymer particles can be improved by additional extrusion, at relatively high temperatures, of polymer gels which have been produced in the polymerization reactor with at least two shafts rotating around parallel axes and which have a relatively high degree of crosslinking. The shear forces arising here lead to rougher polymer particles which, after thermal surface-postcrosslinking, have high swelling rate (FSR) and high centrifuge retention capacity (CRC). However, excessive introductions of energy during extrusion lead to poorer swelling rate (FSR) and poorer centrifuge retention capacity (CRC), and should therefore be avoided. The teaching disclosed in the patent application WO 2014/118024 A1 and the content of WO 2014/118024 A1 are part of this text and are incorporated here by way of reference to WO 2014/118024 A1.

The invention is based on a single-screw extruder according to the preamble of claim 1 for changing a morphology of superabsorbent polymer gel (SAP polymer gel), specifically having:
 an input aperture for the introduction of SAP polymer gel, connected to the input aperture, a channel,
  arranged in the channel, a screw for conveying, and changing the morphology of, the SAP polymer gel and connected to the channel, an output aperture preferably likewise for changing the morphology, for the discharge of the SAP polymer gel with changed morphology.

The screw has a shank and has screw flights arranged on the shank and is arranged and configured to convey the SAP polymer gel from the input aperture to the output aperture by means of the screw flights.

The channel has an input zone arranged at, or in the vicinity of, the input aperture, an output zone arranged at, or in the vicinity of, the output aperture, and a conveying zone extending along the channel from the input zone to the output zone.

Such single-screw extruders are well known from the prior art and serve inter alia for conveying solid or high-viscosity liquid compositions by using the functional principle of a screw conveyor, and for shaping of the composition.

Such single-screw extruders have by way of example a screw which is arranged in a barrel and which typically is rotated around its longitudinal axis by a drive motor.

The screw has screw flights and a shank. The screw flights extend along a longitudinal axis of the shank. The barrel is typically cylindrical, and the screw flights of the screw are therefore adjacent to the barrel wall. The internal space of the barrel can be divided into an input zone, a conveying zone and an output zone, known as metering zone. Composition is typically introduced by way of a hopper and through an input aperture into the input zone of the single-screw extruder. Once composition has been charged to the single-screw extruder, the rotation of the shank of the screw leads to conveying of the composition along the barrel from the input zone by way of the conveying zone to the output zone. Friction is moreover generated between the rotating composition and the stationary barrel wall; pressure can thus be increased, and extrusion can be achieved through a shaping output aperture at the end of the output zone, i.e. downstream of the metering zone, of the single-screw extruder.

This type of abovementioned screw has, alongside other parameters, a pitch G and a shank diameter d, and also an external screw flight diameter D. The pitch is the distance between two screw threads. Screws can be categorized by way of the ratio of shank diameter d to external screw flight diameter D, i.e. d/D. If the ratio d/D is between 0.3 and 0.5, the screw is termed deep-cut and permits high throughput. If the ratio d/D is between 0.7 and 0.9, the screw is termed flat-cut, and can achieve high pressure, but provides lower throughput than the deep-cut screw.

FIG. 1 of EP 1 510 317 B1 shows a screw extruder with an open-top feed aperture, a cylindrical tubular component, and a screw component. The screw component is driven by a motor, and rotates in the cylindrical tubular component. At the front end of the tubular component there is a perforated extrusion plate with a large number of small perforations. The screw component conveys small cut pieces along the tubular component to the perforated extrusion plate. The small pieces are forced through the extrusion plate and molded to give hydrogel particles. According to FIG. 1 thereof, the pitch of the screw is larger in the input zone than in the conveying zone.

FIG. 1 of EP 2 557 095 A1 shows a screw extruder with a cylindrical barrel, a base, a screw, a feed aperture, a hopper, an extrusion aperture, a porous die, a rotational blade, a ring, a backflow-prevention component and a motor. Hydrogel is introduced into the feed aperture from above by way of the hopper into the barrel. The screw is arranged in the barrel. The rotational blade can be arranged on the screw. The motor drives the screw. The screw is used to convey the hydrogel along the screw extruder, and the hydrogel is then passed out of the extrusion aperture via the porous die and the rotational blade. Said FIG. 1 shows that the pitch of the screw is greater in the input zone than in the conveying zone.

JP 2005-272653 A reveals a screw extruder for the processing of a hydrogel with inter alia a barrel, a screw shaft, a feed aperture, an output aperture and a screw. The screw shaft of the screw extruder is configured to prevent backflow of water-containing gel toward the supply side. For this purpose, the screw shaft has lateral section lengths corresponding to the ratio $C=(B/A)\times 100$, where C is in a range between 100% and 500%. A is the lateral section length between the proximal end of the screw and the distal end of the feed aperture, and B is the lateral section length between the distal end of the feed aperture and the distal end of the screw.

JP 2002-177807 A reveals a screw extruder for the processing of a hydrogel with a barrel, a feed aperture, a screw, a rotary cutter and a porous plate. Raw material is introduced into the barrel by way of the feed aperture. The raw material is conveyed along the barrel with the aid of the screw. The rotary cutter is arranged at the end of the screw, between the latter and the porous plate; the raw material can thus be cut and forced out through said plate.

The book "Applied Plastics Engineering Handbook: Processing and Materials" by Myer Kutz, $1^{st}$ edn. 2011 defines on pp. 227 to 267 parameters for a geometry of screws of extruders for plastics processing. Typical screws have a constant helix angle of 17.7° and a constant pitch. FIG. 15.22 of the book reveals the structure of a screw with constant helix angle and constant pitch. The screw has a shank diameter that increases along the longitudinal axis, and constant external screw flight diameter. Another screw with three divisions in each case of constant pitch has constant pitch in each zone: specifically, constant pitch with helix angle 17.7° in an input zone, larger constant pitch in a conveying zone, and constant pitch with helix angle 17.7° in the output zone.

It is an object of the invention to provide an improved single-screw extruder for changing a morphology of superabsorbent polymer, specifically an SAP polymer gel, where specific mechanical energy usage (SME) must be minimized for maximized throughput.

Said object is achieved in the invention by a single-screw extruder for changing a morphology of superabsorbent polymer gel (SAP polymer gel); said extruder has an input aperture, a channel, a screw and an output aperture. The input aperture is configured for the introduction of SAP polymer gel. The channel has connection to the input aperture. The screw is arranged in the channel and is configured for conveying, and changing the morphology of, the SAP polymer gel. The output aperture has connection to the channel, preferably for changing the morphology, for the discharge of the SAP polymer gel with changed morphology. The screw has a shank and screw flights arranged on the shank, and is arranged and configured to convey the SAP polymer gel from the input aperture to the output aperture by means of the screw flights. The channel has an input zone at, or in the vicinity of, the input aperture, an output zone at, or in the vicinity of, the output aperture, and a conveying zone extending along the channel from the input zone to the output zone. The screw has a pitch value of a pitch of the screw flights along the conveying zone of the channel.

According to the invention, the channel has at least one mixing-element arrangement with at least one mixing element which protrudes into the channel of the single-screw extruder and which is configured for the mixing of the SAP polymer gel. The pitch value can advantageously be fixed or vary.

The SAP polymer gel can by way of example comprise a superabsorber, for example a copolymer made of acrylic acid and sodium acrylate. The superabsorbent polymer (SAP) in a dry state takes the form of a powder. A dry state here is a state in which the SAP has not come into contact with liquid, or has been dried. If the SAP has come into contact with liquid, the former swells and forms a hydrogel or polymer gel. The single-screw extruder is configured to convey an SAP polymer gel, for example one that has arisen from a polymerization process, and to change a morphology of said gel. The SAP polymer gel is therefore in a state in which the SAP has come into contact with liquid.

The invention has revealed that high throughput of SAP polymer gel through single-screw extruders known from the prior art typically produces an undesired morphology, or could disrupt a preferred morphology of the SAP polymer gel. A desired morphology of the SAP polymer gel provides improved water absorption, in particular in that the surface porosity and/or the permeability of the SAP polymer gel is increased. It has hitherto been difficult to increase throughput without losing the desired morphology of the SAP polymer gel. One aspect of the invention is that relatively high throughput of SAP polymer gel can be achieved via the single-screw extruder with simultaneous production of SAP polymer gel with a desired morphology.

The invention includes the discovery that it is advantageous to adjust the geometry of the screw of the single-screw extruder in a manner that is appropriate for the SAP polymer gel which is to be conveyed, and the morphology of which is to be changed, and in a manner that minimizes the required specific mechanical energy usage. The single-screw extruder is thus intended for producing a desired morphology which improves water absorption without thereby introducing a large quantity of specific mechanical energy (SME) into the SAP polymer gel. Another aspect of the invention is that it permits high throughput of SAP polymer gel. The invention moreover permits production of durable SAP polymer gel. In particular, the invention can improve the properties of the SAP polymer gel in respect of conveying along the channel. An advantageous polymer morphology can moreover be achieved or maintained, while throughput of SAP polymer gel through the channel can be increased. Another aspect is that less energy usage per unit of material is required, because higher conveying efficiency is possible, and consequently higher throughput can be achieved. The result is therefore the possibility of providing a smaller and more cost-efficient single-screw extruder.

Once the morphology has been changed with the aid of the single-screw extruder, and the SAP polymer gel has a desired morphology, the SAP polymer gel can by way of example be introduced into a drying process for drying of the SAP. It is preferable that the morphology of the SAP polymer gel is changed in a manner that increases the water absorption and/or the absorption rate of the SAP polymer gel. This is by way of example possible in that the surface porosity and/or the permeability is increased. The overall result should be that the water-absorbent polymer particles have high swelling rate and high centrifuge retention capacity together with high permeability.

Other process steps can be applied to the SAP. By way of example, the SAP dried in the drying process can be ground in a grinding process with the aid of a mill, thus giving SAP particles with various sizes. These can then by way of example be sieved with the aid of sieves with various pore apertures; SAP particles with various sizes can thus be separated. The SAP particles of various sizes thus separated can then by way of example be remixed in accordance with desired size mixtures in order to obtain an SAP particle mixture with desired properties, for example with a particular particle size distribution (PSD). Other process steps can then also be carried out for further improvement of the properties of the SAP particle mixture, an example being surface-postcrosslinking or surface crosslinking (SXL). During SXL, other substances are applied to the surface of each SAP particle. The SAP particle mixture with the substances located on the surface is heated to form a network on the surface of the respective particles. This network can by way of example be of assistance in a swollen state, i.e. if the SAP particle mixture has come into contact with a liquid and has assumed the form of an SAP polymer gel, by preserving the shape of the particles and thus increasing retention capability or centrifuge retention capacity for absorbed liquid. In particular, the additional surface network can increase retention capability when the SAP polymer gel is subject to elevated pressure.

Advantageous embodiments of the invention can be found in the dependent claims and provide details of advantageous possibilities of realizing the concept explained above in the context of the objects addressed, and also in respect of other advantages.

It is preferable that the screw has a first pitch value of a pitch of the screw flights along the conveying zone of the channel and, following in conveying direction, has a second pitch value of the pitch of the screw flights along the conveying zone of the channel. The second pitch value is preferably larger than the first pitch value.

In a preferred embodiment, the screw has, along the channel, at least three different pitch values of the screw flights. By way of example, the screw flights can have three different pitch values, of which the first pitch value is the smallest. In this case, the second pitch value is preferably the second smallest, and the third pitch value is the largest. By way of example, the first pitch value can be located in the input zone, and the two other pitch values can be located in the conveying zone. However, it is also possible by way of example that all three different pitch values are located in the conveying zone, where a first pitch value in conveying direction along the channel by way of example can be smaller than a third pitch value in conveying direction along the channel, but larger than a second pitch value in conveying direction along the channel. The pitch can also therefore initially decrease and then in turn increase, or can initially increase and then in turn decrease. The screw can by way of example also have four different pitch values along the channel, e.g. two different pitch values along the input zone and two different pitch values along the conveying zone, i.e. a first pitch value in the input zone can be smaller than a second pitch value that follows in conveying direction. The screw can also have different pitch values in the output zone; in particular, a first pitch value in the output zone can also be smaller than a second pitch value that follows in conveying direction.

In one embodiment, the pitch of the screw flights of the screw changes at least twice along the conveying zone of the channel.

In another preferred embodiment, the pitch of the screw flights increases along the conveying zone of the channel, i.e. a first pitch value located at the transition between the input zone and conveying zone is smaller than all pitch values that follow in conveying direction, and the pitch value located at the transition between the conveying zone and output zone is the largest along the conveying zone. It is therefore preferable that the screw flights have a smallest pitch value along the conveying zone at a transition from the input zone to the conveying zone and a largest pitch value along the conveying zone at a transition from the conveying zone to the output zone. It is particularly preferable that each subsequent pitch value in conveying direction along the conveying zone is larger than or at least as large as the preceding pitch value in conveying direction. The pitch in the conveying zone can by way of example increase linearly, exponentially, or in stepwise fashion along the conveying direction. This permits increase of the volume of the SAP polymer gel present along the conveying zone.

Because the pitch of the screw flights increases along the conveying zone of the channel, the pressure acting on the SAP polymer gel can be decreased along the conveying zone between input aperture and output aperture.

It is preferable that the pitch of the screw flights increases continuously along the conveying zone of the channel. This permits continuous increase of the conveying volume along the conveying zone between input aperture and output aperture. This moreover permits continuous pressure reduction along the conveying zone between input aperture and output aperture. A continuous pressure change permits more homogeneity of the SAP polymer gel production and can improve conveying performance.

According to the invention, the channel of the single-screw extruder has at least one mixing-element arrangement with at least one mixing element which protrudes into the channel of the single-screw extruder and is configured for the mixing of the SAP polymer gel.

The mixing element is preferably arranged within an internal space of the channel. The mixing-element arrangement can extend, or be arranged, along one portion of the channel or over the entire length of the channel. It is preferable that the mixing-element arrangement extends at least along the conveying zone, or is arranged along same. It is preferable that the mixing-element arrangement is arranged at least to some extent around the periphery of the shank of the screw.

The mixing-element arrangement can by way of example have one or more pin arrangements which protrude into the internal space of the channel and are distributed along the entire length of the channel, for example arranged at a plurality of sites along the axis of the screw; a pin arrangement can comprise pins, studs or the like, arranged peripherally around the screw and distributed along the axis of the screw. Alternatively or in addition, a mixing-element arrangement can have one or more cutouts in the screw flights of the screw, said cutouts being distributed along the entire length of the channel, for example arranged at a plurality of sites along the axis of the screw. The pins, studs or the like of the pin arrangement can project into these cutouts at the appropriate site along the axis of the screw. The pins, studs or equivalent mixing elements of a pin arrangement, and corresponding cutouts in the screw, serve, at the site of the pin arrangement, for mixing and for increased shearing of the SAP polymer gel conveyed along the internal space of the channel. It is preferable that the pins are arranged in a wall of the channel, in particular are secured and protrude into the internal space of the channel.

It is particularly preferable that the mixing-element arrangement has at least one pin extending into the internal space of the channel and at least one cutout along the screw flights. Pin and cutout are preferably arranged in a manner such that the pin extends into the cutout of the screw flights when the screw flights are rotated during operation, rotation of the shank of the screw therefore being possible without contact between the pin and the screw flights. Where the screw flight has a cutout, a section of the screw flight of the screw has been removed. It is preferable that a plurality of pins are arranged along the periphery of the internal space of the channel in a manner such that these have the effect of a mesh along the channel in conveying direction. The SAP polymer gel conducted through the mesh formed by the pins can thus be mixed and sheared. The embodiment of the mixing element with pins in cutouts of the screw flights thus permits change of the morphology of the SAP polymer gel in the single-screw extruder. A desired morphology is produced here, having porosity sufficiently high to permit improvement of water absorption ("surface activation"). The pins in these cutouts provide an increased extent of mixing, in particular for single-screw extruders of relatively large dimensions, in particular production-scale versions of the single-screw extruder. For single-screw extruders of smaller dimensions, in particular laboratory-scale versions of a single-screw extruder, it is possible to discern a smaller, but significant, improvement in the extent of mixing, and increased shear.

In a preferred embodiment, the channel has at least two pins arranged along the channel in the conveying direction and separated from one another by a mixing-element separation. A value of the mixing-element separation is preferably adjusted appropriately for a pitch value of the pitch of the screw flights. The manner of adjustment of the mixing-element separation to be appropriate for the pitch is preferably such that a larger value of the mixing-element separation is provided when a larger pitch value is provided, and a smaller value of the mixing-element separation is provided when a smaller pitch value is provided. It is preferable that a plurality of pins are arranged around the periphery of a shank in a manner that forms a channel chamber in the space between the two respectively separately arranged pins. A screw flight chamber is formed between two screw threads, i.e. with the length of the pitch. The length of the channel chamber can be adjusted appropriately for the length of the screw flight chamber. The lengths are preferably positively correlated, i.e. the length of the channel chamber increases with increasing pitch. In one embodiment, the length of the channel chamber increases along the conveying zone in conveying direction, for example linearly, exponentially, or in equivalent manner.

In another embodiment, the single-screw extruder can have screw flights with at least one pitch value of the screw flights that is between 30 mm and 800 mm, for example between 500 mm and 600 mm. The screw flights can by way of example have a first pitch value of 500 mm, a second pitch value of 550 mm, and a third pitch value of 600 mm. The screw flights can by way of example also have only two different pitch values, for example 500 mm and 600 mm. The pitch values of the screw flights can also change continuously along the channel between 30 mm and 800 mm, in particular between 500 mm and 600 mm. By way of example, the pitch can change continuously along the channel in that the pitch value increases from 500 mm in the vicinity of the input aperture to 600 mm in the vicinity of the output aperture.

It is preferable that the single-screw extruder has a value of a flight land width of the screw flights between 4 mm and 80 mm, for example 40 mm.

In one embodiment, the single-screw extruder can have at least one value between 25 mm and 500 mm, for example 310 mm for a channel depth between the shank of the screw and a wall of the channel.

It is preferable that the single-screw extruder has a value of an external screw flight diameter between 60 mm and 1000 mm, for example 650 mm. It is preferable that the single-screw extruder has at least one value of a shank diameter between 25 mm and 500 mm, for example 340 mm.

The ratio of shank diameter to external screw flight diameter in the single-screw extruder is preferably between 0.4 and 0.6, for example between 0.449 and 0.577. The ratio of shank diameter to external screw flight diameter in the single-screw extruder is particularly preferably 0.52. The single-screw extruder can also have a ratio of shank diameter to external screw flight diameter between 0.3 to 0.9. The ratio of the shank diameter to external screw flight diameter determines the ratio of throughput to pressure acting on the SAP polymer gel. A larger ratio of shank diameter to external screw flight diameter brings about higher pressure and lower throughput, because transport volume is reduced. When the screw is in operation, defined screw-flight chambers form by virtue of the pitch between the screw threads, with available transport volumes increasing along the channel. The increasing available transport volumes are a consequence of the increasing pitch values in conveying direction along the conveying zone.

In a preferred embodiment, the pitch increases along the conveying zone from a pitch value of 500 mm in the vicinity of the input zone to a pitch value of 600 mm in the vicinity of the output zone. By virtue of the increasing pitch it is possible to increase the available transport volume of the screw-flight chamber, while the pressure acting on the SAP polymer gel is simultaneously reduced.

In another preferred embodiment, the screw has, along the channel, a smallest pitch value that is at most between 20% and 85% of a largest pitch value along the channel. The screw can by way of example have, in the vicinity of the input zone, a pitch value that is at most between 20% and 85% of a pitch value in the vicinity of the output zone. The restriction of the change of pitch along the channel reduces the risk that an undesired morphological change of the SAP polymer gel will occur.

The single-screw extruder is preferably configured to produce an SAP polymer gel with a desired morphology that increases the water absorption of the SAP, and with throughput at least 23 metric tons per hour. The single-screw extruder is accordingly dimensioned as production-scale version for this purpose; this means that the size of, inter alia, the channel and the screw is appropriate.

In a particularly preferred embodiment, the single-screw extruder has a drive motor and/or a heating device. The drive motor is preferably configured to rotate the shank of the screw at up to 150 revolutions per minute, for example at 75 revolutions per minute and preferably at 30 revolutions per minute.

The heating device is preferably configured to heat the channel so that the temperature thereof is between 85° C. and 140° C., at least in the input zone. The heating device can by way of example extend along the length of the channel and enclose same, thus permitting uniform heating. Alternatively, the heating device can also extend only over portions of the channel. The heating device can also be arranged and configured in a manner such that it can produce various temperature zones.

It is preferable that the heating device is arranged and configured in a manner such that during operation of the single-screw extruder the temperature of the SAP polymer gel in the channel increases along the conveying direction as far as an output zone, preferably by a temperature in the range from 20° C. to 40° C. The temperature increases with energy input, and in particular via increase of pressure and shear forces along the conveying direction. It is moreover preferable that directly after the output aperture the cooled SAP polymer gel has a reduced temperature between 90° C. and 110° C.

The heating device preferably comprises an oil at a temperature of up to 150° C. The heating device can also be configured for cooling and for this purpose can by way of example comprise an oil at a temperature that is lower than the temperature of the SAP polymer gel.

In one embodiment, the length of the channel is between 200 mm and 4000 mm. The length of the channel is preferably at least 3000 mm, the effective length of the screw therefore being 3000 mm. The internal diameter of the channel can by way of example be between 50 mm and 750 mm. The internal diameter of the channel is preferably 650 mm.

In a preferred embodiment, the output aperture comprises a die, preferably likewise for changing the morphology, for the discharge of the SAP polymer gel with changed morphology. The die can have an open passage or a perforation or a plurality of open passages or perforations, or can in principle have a number of open passages or perforations in the range between 60 and 90—this being a preferred number of perforations for the laboratory-scale version of the single-screw extruder. A production-scale version of the die preferably has very many more perforations. The die particularly preferably has more than 1000 perforations, for example 3600 perforations. The die in the production-scale version of the single-screw extruder preferably has a number of perforations in the range between 3000 and 4000.

Diameters of the perforations can by way of example be between 4 mm and 12 mm. The diameter of the perforations is preferably 8 mm. It is preferable that 10% of the area of the die is open, i.e. that areas of open passages or of perforations provide 10% of said area.

In a preferred embodiment, the output aperture comprises a die with 3000 perforations, the diameter of each of which is 8 mm. In this case it is preferable that 10% of the area of the die is open.

In a preferred embodiment, the single-screw extruder is configured to generate a maximal pressure of 50 bar. The single-screw extruder can be configured to produce a throughput of 30 t/h (metric tons per hour). The single-screw extruder can moreover be configured to absorb a specific mechanical energy of up to 60 kWh per metric ton. The single-screw extruder can moreover be configured to operate with power input of up to 18.5 kW.

The invention moreover provides a process for changing the morphology of a superabsorbent polymer gel (SAP polymer gel), with the single-screw extruder of the invention or with one of the embodiments. The process has the following steps:
  introduction of the SAP polymer gel from a polymerization process into the single-screw extruder,
  operation of the single-screw extruder in order to change the morphology of the SAP polymer gel and
  discharge of the SAP polymer gel with changed morphology from the single-screw extruder to a drying process.

In one embodiment of the process, the drying process comprises the following steps:
  distribution of the SAP polymer gel with changed morphology on metal drying sheets and
  heating of the SAP polymer gel with changed morphology on the metal drying sheets in a convection oven.

Various quantities of SAP polymer gel with changed morphology can be charged to the metal drying sheets; the charge level therefore depends on the area of the metal drying sheet and on the quantity of the SAP polymer gel with changed morphology charged to the metal drying sheet. The drying temperature and drying time depend on the charge level; by way of example a drying temperature of 175° C. can be used for 70 minutes for a charge of 0.91 g/cm². The metal drying sheets can comprise a sieve tray, for example with 250 μm mesh apertures, so that the liquid can also escape through the sieve tray. The sieve tray can by way of example be composed of wires, the diameter of each wire being 130 μm.

In one embodiment, the process has the following additional step:
  introduction of the dried SAP into a grinding process.

It is preferable that, in the grinding process, the dried SAP is ground by a mill in a manner that produces SAP particles with different sizes.

The process can moreover have the following step:
  introduction of the ground SAP into a sieving process or classification process.

It is preferable that, in the sieving process or classification process, the ground SAP is sieved or classified in a manner that separates SAP particles with various sizes from one another.

The process can moreover have the following step:
  introduction of classified SAP particles into a mixing process.

It is preferable that, in the mixing process, SAP particles of various sizes are mixed in accordance with a predetermined mixing ratio in order to obtain desired properties of the SAP particle mixture.

The process can moreover have the following step:
  introduction of the SAP particle mixture into a surface-postcrosslinking process or surface crosslinking (SXL) process.

It is preferable that a surface-crosslinking substance, which can by way of example comprise isopropanol, water and/or aluminum lactate, is applied to the surface of the SAP particles. The SAP particles wetted with surface-crosslinking substance are then preferably heated at a temperature of 185° C. in a manner that brings about surface crosslinking on the respective SAP particles. The surface crosslinking allows the SAP particles to maintain their shape in the swollen state, i.e. when the SAP particles have absorbed liquid and take the form of polymer gel. In particular, the surface crosslinking can increase retention capability for absorbed liquid under pressure.

The invention moreover provides the use of the single-screw extruder of the invention, or of one of the embodiments, for changing a morphology of superabsorbent polymer gel (SAP polymer gel).

Working examples of the invention are now described below with reference to the drawing. The latter is not necessarily intended to depict the working examples to scale; instead, where this is helpful for explanation purposes, the drawing is diagrammatic and/or intentionally slightly distorted. Reference is made to the relevant prior art for information supplementary to the teachings directly apparent from the drawing. A point requiring attention here is that a wide variety of modifications and changes relating to the form and detail of a working example can be made without departing from the general concept of the invention. The inventive features disclosed in the description, in the drawing and in the claims can be significant not only individually but also in any desired combination for embodiments of the invention. The scope of the invention moreover includes all combinations of at least two of the features disclosed in the description, the drawing and/or the claims. The general concept of the invention is not limited to the precise form, or the detail, of the preferred working examples revealed and described below; nor is it limited to any subject matter that would be more restricted than the subject matter claimed in the claims. When ranges are stated, values lying within the boundaries specified are also intended to be disclosed as boundary values and to be usable and claimable as desired. In the interests of simplicity, identical reference signs are used below for identical or similar components or components with identical or similar function.

Further advantages, features and details of the invention will be apparent from the description below of the preferred working examples, and also with reference to the drawing; the latter shows in.

Figure 1:
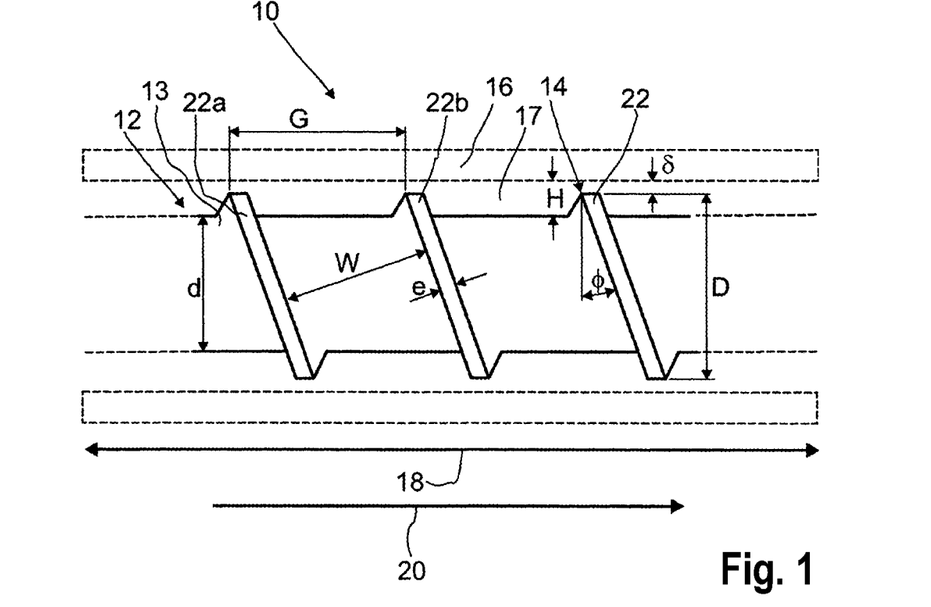
FIG. 1 a diagram of a detail of an example of a single-screw extruder with a screw, with parameter definitions.

FIG. 1 shows a detail of a single-screw extruder 10 with a screw 12. The screw 12 has a shank 13, and also screw flights 14 extending along the shank 13, and is arranged in an internal space 17 of a channel 16. The detail shown in FIG. 1 shows a section, arranged in a conveying zone 18, of the screw 12. The conveying direction 20 along the conveying zone 18 runs from left to right in this depiction.

During operation of the screw 12, the shank 13 rotates around its longitudinal axis; the screw flights 14 therefore also rotate, and the screw threads 22 convey material, for example SAP polymer gel 24 (see FIG. 2), along the channel 16 in conveying direction 20. The material here, for example SAP polymer gel 24, is firstly subject to pressure from the screw flights 14 and from the wall of the channel 16, but secondly is also subject to tension; the resultant flow behavior is therefore complex. The conveying zone 18 therefore functions as pump which conveys material, for example SAP polymer gel 24, from an input zone 26 to an output zone 28 (see FIG. 2). An advantageous pressure value in the output zone 28 is sufficiently high to force the SAP polymer gel 24 out from the output aperture 30 via a perforated plate 32 and a die 34 (see FIG. 2), i.e. preferably to change the morphology of the SAP polymer gel 24. The magnitude of the advantageous pressure value depends inter alia on the quantity of material, the viscoelastic properties of the material, for example the SAP polymer gel 24, and the temperature thereof.

The pressure, and throughput of the material, for example SAP polymer gel 24, can be adjusted as required by the parameters of the screw 12, in particular of shank 13 and screw flights 14. The throughput and pressure moreover depend inter alia on the rotational velocity of the shank 13 of the screw 12. Particular advantageous pressures are required for the change of morphology of the SAP polymer gel 24. It can therefore be necessary to adjust the parameters of the screw 12, in particular of shank 13 and screw flights 14, in a manner that achieves a sufficiently high pressure.

Parameters of the single-screw extruder 10 are the shank diameter d (frequently also termed root diameter), the external screw flight diameter D, the pitch G (frequently also termed lead), channel width W, flight land width e (frequently also termed flight width), channel depth H (frequently also termed metering depth), helix angle $\phi$, and the distance $\delta$ from the wall of the channel 16 (frequently also termed flight clearance). These parameters are explained in more detail below.

The shank 13 of the screw 12 has the diameter d. The screw flights 14 have the external screw flight diameter D. The screw flights 14 of the screw 12 can be categorized via the ratio of shank diameter d to external screw flight diameter D, i.e. d/D. If the value d/D is between 0.3 and 0.5, the screw is termed deep-cut and permits high throughput. If the value d/D is between 0.7 and 0.9, the screw is termed flat-cut, and can achieve high pressure, but provides lower throughput than the deep-cut screw. The throughput of the screw, in particular of a flat-cut screw, can be increased by increasing the rotational velocity of the shank 13 of the screw 12. It is therefore possible for a flat-cut screw to achieve high pressure with relatively high throughput. However, this requires relatively high energy usage in order to provide the high rotation rates of the shank 13 of the screw 12 that are required for this purpose.

The pitch G of the screw flights 14 is the distance between the proximal side of a first screw thread 22a and the proximal side of a second screw thread 22b of the screw flights 14. The channel width W is the distance between the distal side of a first screw thread 22a and the proximal side of a second screw thread 22b of the screw flights 14. The flight land width e is the width of the screw flight 14. The channel depth H is the distance between the wall of the channel 16 and the surface of the shank 13. The helix angle $\phi$ is the angle of inclination of the screw flight 14. The distance $\delta$ from the wall of the channel 16 is the distance between the external surface of the screw flight 14 and the wall of the channel 16. A minimal distance $\delta$ from the wall of the channel 16 should be maintained, because otherwise during operation the screw flights 14 could drill into the wall of the channel 16 and damage same. However, the distance $\delta$ from the wall of the channel 16 is very small in comparison to the other dimensions, for example less than 1 mm.

Figure 2:
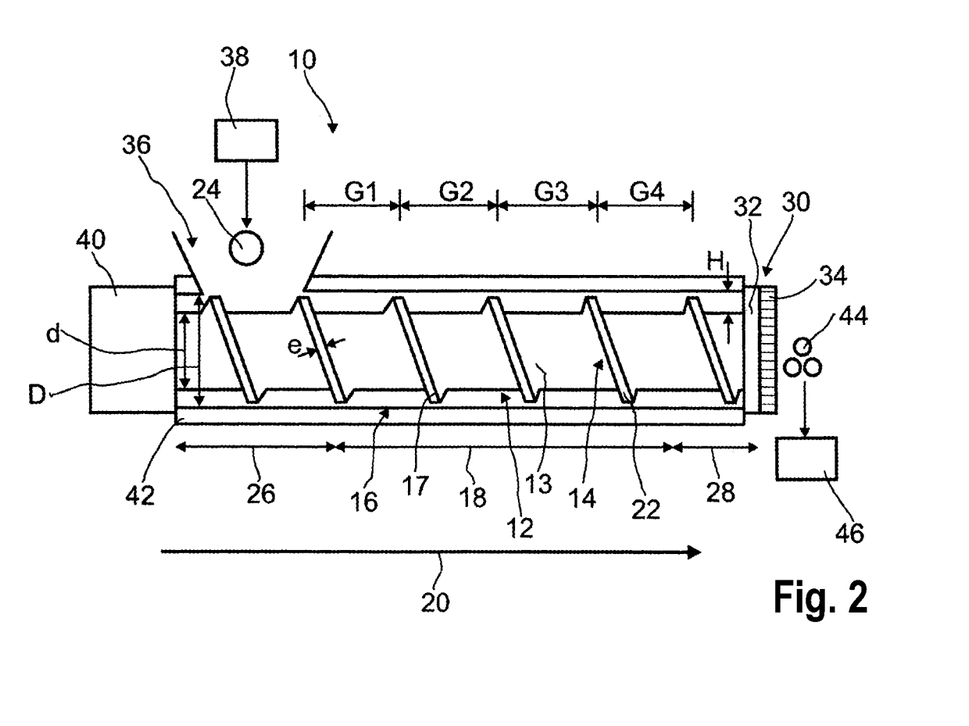
FIG. 2 a diagram of an embodiment of a single-screw extruder in a preferred working example as in the concept of the invention with, not shown here, mixing elements of a mixing-element arrangement.

FIG. 2 shows a preferred working example of a single-screw extruder 10. This can have various dimensions, an example being a large production-scale version of the single-screw extruder 10 suitable for industrial production, or as a small laboratory-scale version of the single-screw extruder 10 serving for experimental purposes. The structure of the two versions of the single-screw extruder 10 is identical. The single-screw extruders 10 differ primarily in their dimensions. In particular, the large production-scale version of the single-screw extruder 10 is configured for throughput up to 30 metric tons per hour, whereas the laboratory-scale version of the single-screw extruder 10 is configured only for throughput up to 340 kg/h (kilograms per hour). The laboratory-scale version of the working example of the single-screw extruder 10 is a smaller-scale version of the production-scale version of the working example of the single-screw extruder 10, and can in particular be used for experimental purposes, for example in order to make comparative measurements for various screws 12.

The single-screw extruder 10 has an input aperture 36, a channel 16, a screw 12 and an output aperture 30. The channel 16 has an internal space 17, comprising an input zone 26, a conveying zone 18 and an output zone 28, and extending between the input aperture 36 and the output aperture 30. The single-screw extruder 10 can be used to convey a superabsorbent polymer gel (SAP polymer gel 24) in conveying direction 20 and to change a morphology of the SAP polymer gel 24. In particular, the single-screw extruder 10 can be used to increase the surface porosity of the particles of the SAP polymer gel, in order to increase the water-absorption capability of the SAP polymer gel.

In a preferred working example of the single-screw extruder 10 in FIG. 2, this single-screw extruder 10 as in the concept of the invention has a mixing element, not shown in this figure. The mixing element can—as in FIG. 3, and with identical function and advantage—have pins in the channel 16 and cutouts in the screw flights 14 of the screw 12.

The SAP polymer gel 24 is produced in a polymerization process 38. For the working example shown in FIG. 2, the main polymer on which the SAP polymer gel 24 is based is produced in accordance with the formula shown in table 1.

TABLE 1

| | |
|---|---|
| Reactor | ORP 250 |
| Solid constituents | 42.7% by weight |
| Degree of neutralization | 71 mol % |
| Small-quantity addition of main polymer | 7.7% by weight baP (based on polymer) |
| Hydrogen peroxide | 0.0008% by weight baA (based on acrylic acid) |
| Ascorbic acid | 0.0023% by weight baA |
| Sodium persulfate | 0.128% by weight baA |
| Core crosslinking agent | 0.39% by weight baA (Laromer PO9044V) |
| Monomer temperature | 35° C. |
| Throughput | 800 kg/h |
| Dam height | 160 mm |

The single-screw extruder 10 of FIG. 2 is not limited to the production of SAP polymer gel 24 with the composition of table 1, and can also be used for other compositions of an SAP polymer gel 24.

The SAP polymer gel 24 produced in the polymerization process 38 is introduced by way of the input aperture 36 into the single-screw extruder 10. The input aperture 36 has connection to the internal space 17 of the channel 16, and is adjacent to the input zone 26. During operation of the single-screw extruder 10, the SAP polymer gel 24 is introduced by way of the input aperture 36 of the input zone 26 of the internal space 17 of the channel 16.

The screw 12, which has a shank 13 with screw flights 14, is arranged in the internal space 17 of the channel 16. When the single-screw extruder 10 is operated, the shank 13 of the screw 12 is rotated around its longitudinal axis. For this purpose, a drive motor 40 is provided, which has connection to the shank 13 of the screw 12. In this working example, the drive motor 40 can rotate the shank 13 of the screw 12 at up to 150 revolutions per minute. During operation, the shank 13 is preferably rotated at a rotational velocity appropriate for the dimensions of the single-screw extruder 10: between 30 revolutions per minute for the production-scale version of the single-screw extruder 10 and 75 revolutions per minute for the laboratory-scale version of the single-screw extruder 10. The screw 12 serves, with the aid of the screw flights 14 and of the wall of the channel 16, to convey the SAP polymer gel 24 from the input aperture 36 along the conveying zone 18 to the output aperture 30, and to change the morphology of the SAP polymer gel 24.

In this working example, a heating device 42 completely encloses the channel 16 of the single-screw extruder 10. Alternatively, it is also possible that the heating device 42 encloses only a portion of the channel 16, or that no heating device 42 at all is present (not shown). It is preferable that a heating device 42 encloses the laboratory-scale version of the single-screw extruder 10, whereas the production-scale version of the single-screw extruder 10 is preferably configured without heating device 42. The heating device 42 serves to heat the channel 16. For this purpose, there is an oil arranged in the heating device 42; the temperature of said oil can be up to 200° C.

The heating device 42 is preferably operated in a manner such that the temperature of an SAP polymer gel 24 in the channel 16, at least in the input zone 26, is between 85° C. and 100° C. in the laboratory-scale version of the single-screw extruder 10 and/or somewhat higher in the production-scale version. In the production-scale version of the single-screw extruder 10, the temperature in the channel 16, at least in the input region, is preferably between 90° C. and 140° C. The temperature increases with energy input, in particular via increase of pressure and shear forces along the conveying direction 20. This temperature increase along the conveying direction 20 between the input zone 26 and an output zone 28 can be between 20° C. and 40° C.

It is preferable that the temperature of the SAP polymer gel 24 directly after the output aperture 30 is in turn lower as a consequence of cooling: between 78° C. and 110° C., preferably between 90° C. and 110° C.

The heating device 42 can also be used for cooling, for example if it comprises an oil whose temperature is lower than the temperature of the channel 16 and/or of the SAP polymer gel 24. The heating device 42 can in principle also serve for temperature regulation.

The output aperture 30 has connection to the internal space 17 of the channel 16, and is adjacent to the output zone 28. The output aperture 30 has a perforated plate 32 and a die 34 arranged downstream of the perforated plate 32. The output aperture 30 serves to change the morphology of the SAP polymer gel 24 and to discharge the SAP polymer gel 44 with changed morphology. For this purpose, SAP polymer gel 24 is forced by pressure through the perforated plate 32 and through the die 34 with the aid of the conveying mechanism provided by the screw flights 14 and the wall of the channel 16.

The die 34 in this working example has 66 open passages or in principle can have a number of open passages in the range between 60 and 90; the number in this case is a preferred number of perforations for the laboratory-scale version of the single-screw extruder 10. The die 34 can also have only one open passage or one perforation, or a different number of perforations. By way of example, a preferred number of perforations for the production-scale version of a single-screw extruder will be at least 1000, for example 3600. The die 34 in the production-scale version of the single-screw extruder 10 has a number of perforations in the range between 3000 and 4000.

The diameter of each perforation is 8 mm. Alternatively, the diameter of the perforations can also by way of example be between 4 mm and 12 mm. There can be perforations with diameters of identical size or diameters of various sizes arranged alongside one another. In this working example, for the laboratory-scale version of the single-screw extruder 10 about 66% of the area of the die 34 is open. Alternatively, it is also possible by way of example that between 5% and 66% of the area of the die 34 is open (not shown). In the production-scale version of the single-screw extruder 10, 10% of the area of the die is open (not shown).

The single-screw extruder 10 can additionally or alternatively have, at the output aperture 30, in addition to the perforated plate 32 and the die 34, an adapter, a retainer, a matrix or a combination of these components (not shown). One or more of the abovementioned components can by way of example be arranged at the distal end of the screws 12.

The SAP polymer gel 44 with changed morphology discharged from the output aperture 30 is introduced into a drying process 46. The drying process 46 serves to remove the liquid from the SAP polymer gel 44 with changed morphology, in order to dry same. Various drying processes 46 are conceivable and known to the person skilled in the art. A possible drying process 46 is explained in more detail in the context of the process described in FIG. 4. Further process steps can also follow the drying process 46 (not shown).

Further details of the screw flights 14 and shank 13 of the screw 12 of this working example of the single-screw extruder 10 are explained below.

The screw flights 14 of the screw 12 have a pitch G that increases along the conveying zone 18 of the channel 16. In this working example, the pitch increases continuously. Alternatively, but less preferably, the pitch could also decrease (not shown) at least along a section of the conveying zone 18. The pitch can also initially increase and then in turn decrease, or initially decrease and then in turn increase (not shown). The pitch can also change discontinuously or in stages, for example preferably increase discontinuously or in stages (not shown). It can be seen that the respective sections shown of the screw threads 22 of the screw flights 14 give the different pitch values G1, G2, G3 and G4.

The first pitch value G1 of the pitch in this working example of the laboratory-scale version of the single-screw extruder is 46 mm, and the fourth pitch value G4 is 70 mm, and therefore the pitch G increases along the conveying zone from a pitch value of 46 mm in the vicinity of the input zone to a pitch value of 70 mm in the vicinity of the output zone.

For the production-scale version of the single-screw extruder 10, the first pitch value G1=500 mm and the fourth pitch value G4 is 650 mm. The second and third pitch values G2 and G3 lie between these values. For the laboratory-scale version G2=54 mm and G3=62 mm.

For the production-scale version of this working example G2=550 mm and G3=600 mm. In an alternative working example, not shown, it is also possible by way of example that the pitches G lie between pitch values of 30 mm and 800 mm.

The different pitch values G1, G2, G3, G4 of the pitch are associated with different helix angles φ1, φ2, φ3 and φ4 (not shown).

The value of the flight land width e of the screw flights 14 in this working example of the laboratory-scale version of the single-screw extruder 10 is constant at 6 mm, and for the production-scale version of the single-screw extruder 10 it is constant at 40 mm. The flight land width of the screw flights 14 can also alternatively by way of example have values between 4 mm and 80 mm, and can change along the channel 16, for example can increase or decrease, in particular continuously increase or decrease.

In this working example, the shank 13 of the screw 12 has a constant shank diameter d at least along the conveying zone 18, but preferably additionally through the input zone 26 and/or output zone 28. The constant shank diameter d here has a value of 35 mm for the laboratory-scale version of the single-screw extruder 10, and the constant shank diameter d here has a value of 340 mm for the production-scale version of the single-screw extruder 10. In particular, the shank diameter d can also have values between 25 mm and 500 mm, for example between 340 mm and 380 mm.

The value of the external screw flight diameter D in this working example is 78 mm for the laboratory-scale version of the single-screw extruder 10, and 650 mm for the production-scale version of the single-screw extruder 10. In particular, the external screw flight diameter D can also have values between 60 mm and 1000 mm, for example between 600 mm and 700 mm. In this working example, the ratio of the shank diameter d to external screw flight diameter D is constant and is about 0.449 for the laboratory-scale version of the single-screw extruder 10 and 0.52 for the production-scale version of the single-screw extruder 10. In particular, the ratio of the shank diameter d to the external screw flight diameter D can also lie between 0.4 and 0.6, for example between 0.449 and 0.577, or else in particular between 0.52 and 0.58.

The value of the channel depth H between the shank 13 of the screw 12 and a wall of the channel 16 in this working example is 43 mm for the laboratory-scale version of the single-screw extruder 10 and 310 mm for the production-scale version of the single-screw extruder 10. Alternatively, the channel depth H can also have values between 25 mm and 500 mm, for example between 270 mm and 310 mm.

The working example of the laboratory-scale version of the single-screw extruder 10 is based on an ECT EXR T80. Table 2 below provides an overview of parameters of the working example of the laboratory-scale version of the single-screw extruder 10 and of the production-scale version of the single-screw extruder 10, and also data relating to preferred parameter ranges for single-screw extruders 10.

TABLE 2

| Parameter | ECT EXR T80 (laboratory-scale version) | Single-screw extruder (production-scale version) | Parameter range |
| --- | --- | --- | --- |
| Effective screw length (ESL) | 300 mm | 3000 mm | 200 mm to 4000 mm |
| Internal diameter of channel (IDC) | 80 mm | 650 mm | 50 mm to 750 mm |

TABLE 2-continued

| Parameter | ECT EXR T80 (laboratory-scale version) | Single-screw extruder (production-scale version) | Parameter range |
| --- | --- | --- | --- |
| IDC/ESL | 3.75 | 4.6 | 2.22 to 8 |
| Maximal pressure | 50 bar | 50 bar | 30 to 70 bar |
| Rotational velocity during operation | 75 revolutions/minute | 30 revolutions/minute | 15 rpm to 150 rpm |
| Thickness of die | 33 mm | 33 mm | 20 mm to 45 mm |
| Die perforation diameter | 8 mm | 8 mm | 4 mm to 12 mm |
| Number of die perforations | 66 | 3600 | 1 to 4000 |
| Relative open area of die | 66% | 10% | 5% to 66% |
| Max. throughput | ~340 kg/h | 30 t/h | 200 kg/h to 30 t/h |
| Max. specific mechanical energy consumption | ~60 kWh/t | ~60 kWh/t | 20 kWh/t to 100 kWh/t |
| Temperature of oil in heating device | 150° C. | no oil heating | 80° C. to 200° C. |
| Temperature in channel | ~85-95° C. | 95-140° C. | |
| SAP polymer gel temperature at output aperture | ~78-90° C. | 90-110° C. | |

The single-screw extruder 10 is not limited to the parameters stated in table 2; these merely represent a preferred parameter range.

Figure 3:
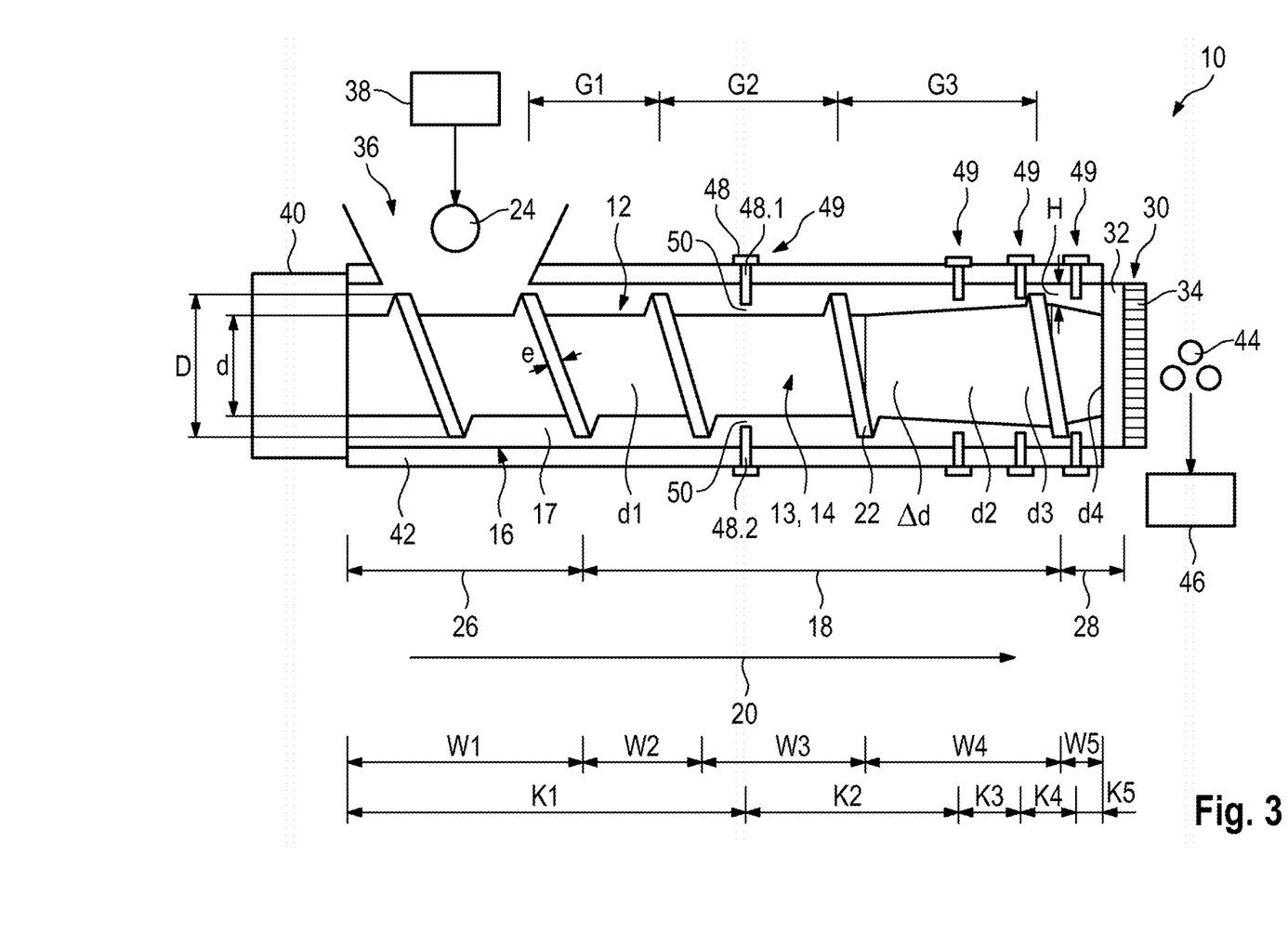
FIG. 3 a diagram of another preferred embodiment of a single-screw extruder as in the concept of the invention with mixing elements of a mixing-element arrangement.

FIG. 3 shows another preferred working example of a single-screw extruder 10. This other preferred working example of the single-screw extruder 10 preferably relates to a production-scale version. The single-screw extruder 10 can in principle also be configured as laboratory-scale version (not shown). The single-screw extruder 10 of this other preferred working example is similar to the working example shown in FIG. 2 of the single-screw extruder 10; identical reference signs are therefore, for reasons of simplicity, used for similar or identical components or components of similar or identical function. In this depiction, the conveying direction 20 along the conveying zone 18 again runs from left to right.

The single-screw extruder 10 has an input aperture 36, a channel 16, a screw 12 and an output aperture 30. The channel 16 has an internal space 17, comprising an input zone 26, a conveying zone 18 and an output zone 28, and extending between the input aperture 36 and the output aperture 30. The single-screw extruder 10 can be used to convey a superabsorbent polymer gel (SAP polymer gel) 24 in conveying direction 20 and to change a morphology of the SAP polymer gel 24.

In this working example, a heating device 42 again completely encloses the channel 16 of the single-screw extruder 10. The heating device 42 can comprise an oil with a predetermined temperature, in order to set a desired temperature in the internal space 17 of the channel 16.

The single-screw extruder 10 of the preferred working example of FIG. 3 resembles the single-screw extruder 10 of the working example of FIG. 2 in that SAP polymer gel 24 charged thereto derives from a polymerization process 38. This is introduced by way of the input aperture 36 into the internal space 17 of the single-screw extruder 10, and conveyed along the channel 16 in conveying direction 20 by the screw threads 22 of the screw flights 14 of the screw 12.

During conveying along the channel 16, the morphology of the SAP polymer gel is changed; in particular, the porosity of the surface of the particles of the SAP polymer gel is increased. At the output aperture 30, the SAP polymer gel is forced through the perforated plate 32 and the die 34, depicted diagrammatically, and the morphology is further changed in a manner that produces an SAP polymer gel 44 with changed morphology. The SAP polymer gel 44 with changed morphology is then introduced into a drying process 46. Other processes (not shown) can then follow after the drying process 46.

This other preferred working example of the single-screw extruder 10 of FIG. 3 differs in essence from the working example of the single-screw extruder 10 of FIG. 2 in that the single-screw extruder 10 of FIG. 3 has a mixing-element arrangement 49 with in each case two mixing elements shown here in the form of pins 48.1 and 48.2 of a pin arrangement 48, and in that the shank diameter d of the shank 13 changes along the channel 16; in this case by way of example it increases. The shank 13 of the screw 12 here has an increasing shank diameter d at least along the conveying zone 18, and preferably additionally through the input zone 26 and/or output zone 28.

Although a working example of a single-screw extruder 10 of FIG. 2—with mixing-element arrangement 49 and constant shank diameter d—is not explicitly shown here, this would likewise be in accordance with the general concept of the invention.

In the second working example of the single-screw extruder 10 of FIG. 3, the mixing-element arrangement 49 here also has four pin arrangements 48 with pins 48.1, 48.2 shown here in the channel 16, and optionally cutouts 50 in the screw flights 14 of the screw 12. Variants of the pin arrangements 48 are shown by way of example in FIG. 4.

In this working example of the single-screw extruder 10, the pins 48.1, 48.2 are secured in the wall of the channel 16 and protrude into the internal space 17 of the channel 16. The pins 48.1, 48.2 of a pin arrangement are arranged around the entire periphery of the channel 16, thus forming a ring of pins around the periphery, of which two pins 48.1, 48.2 are shown here. The pins 48.1, 48.2 of a pin arrangement here are arranged in a manner such that their separation from one another along the periphery is small, and therefore the pin rings made of pins 48.1, 48.2 of one or more pin arrangements 48 together form a mesh-like structure, or a mesh, of a mixing-element arrangement 49.

In practical terms, a channel chamber is formed between each pair of pin rings arranged along the conveying direction 20 and separated by a mixing-element separation K, and made of pins of a pin arrangement 48.

The length of each channel chamber is defined via the value of the pin separations K1, K2, K3, K4, K5, and it varies in this working example because the pin arrangements 48 are arranged with various pin separations K. The first channel chamber along the conveying direction 20 has a value K1 of the mixing-element separation, and is formed by a wall of the channel 16 and by the first pin ring of a pin arrangement 48 with pins 48.1 and 48.2. The first channel chamber extends from the input zone 26 into the conveying zone 18. The channel chambers that follow in conveying direction 20 are formed in the conveying zone 18 between the respective pin rings of a further pin arrangement 48, which can be seen but is not described in any great detail, consisting of further pins 48.1, 48.2 which can be seen but are not described in any great detail; said chambers have the values K2, K3 and K4 for the pin separations. The channel chamber at the output zone 28 of the channel 16 is formed between the final pin arrangement 48 in conveying direction 20 and the perforated plate 32 by way of a pin separation K5.

Figure 4:
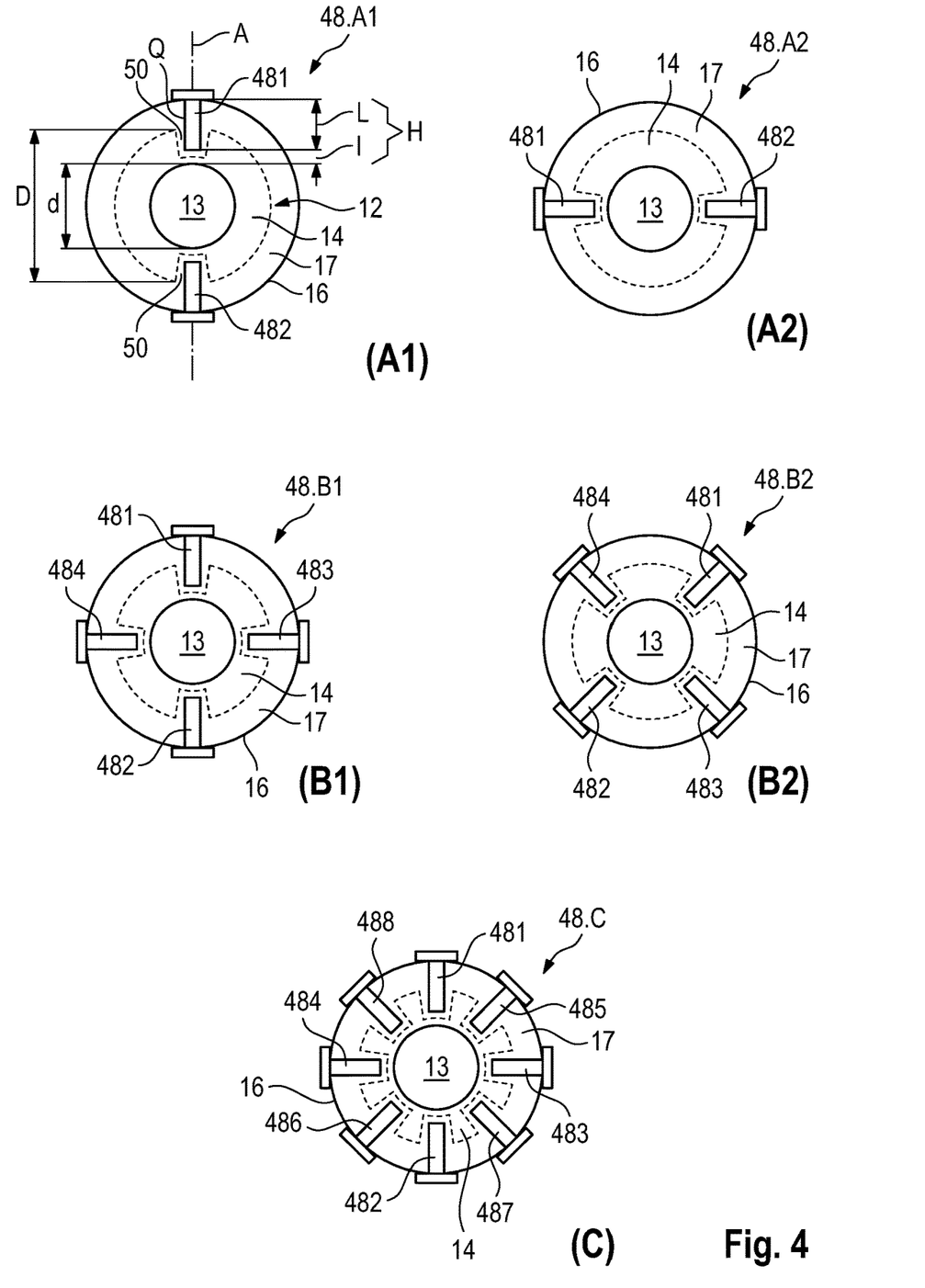
FIG. 4 in views (A1, A2), (B1, B2) and (C), preferred variants of pin arrangements with pins for a mixing-element arrangement shown in FIG. 3 or for a mixing-element arrangement in the embodiment of FIG. 2.

The cutouts 50 that can be seen in FIG. 4 in the screw flights 14 are arranged in a manner such that during operation when the shank 13 is rotated by way of the drive motor 40 the pins 48.1, 48.2 pass through the cutouts 50 during rotation of the shank 13, without any contact between the pins 48 and the screw flights 14. The cutouts 50 therefore constitute interruptions in the screw flights 14.

The pins 48.1, 48.2 of a pin arrangement 48 and the cutouts 50 serve for mixing and shear of the SAP polymer gel 24. Improved mixing and increased shear is apparent in particular in the case of a production-scale version of the single-screw extruder 10, i.e. a version with relatively large dimensions. The mixing-element arrangement 49 has less effect in the case of a laboratory-scale version with smaller dimensions.

In this working example of the single-screw extruder 10, the shank 13 of the screw 12 is divided into five shank segments W1, W2, W3, W4 and W5. The shank segment W1 lies within the input zone 26, the shank segments W2, W3 and W4 lie within the conveying zone 18, and the shank segment W5 lies within the output zone 28. The shank segments W1 to W5 have a shank diameter d with an initial value d1=340 mm. The shank segment W3 has a shank diameter that changes continuously from the initial value d1=340 mm to a second value d2=380 mm—i.e. by Δd. In the shank segments W4 and W5, the shank diameter initially has the value d2=380 mm and then remains at d2 or (as here) then increases further to d3>380 mm. In the shank segment W5, i.e. in the output zone 28, the shank diameter d decreases continuously from the value d2=340 mm or d3>380 mm to a value d4=120 mm.

The output zone 28 therefore has a greater transport volume; it is thus possible to use less pressure to force a greater quantity of SAP polymer gel through the output aperture 30.

In the screw 12 in this working example, the lowest value of a shank diameter d1 along the channel 16 is about 32% of the highest value of the shank diameter d2 or d3 along the channel 16. The lowest value of the shank diameter d along the channel 16 can also be at most between 20% and 80% of a highest value of a shank diameter along the channel 16. The value of the external screw flight diameter D is constant along the channel 16 and is 650 mm. The ratio d/D of shank diameter d to external screw flight diameter D is therefore d/D=0.52 along the conveying zone 18 of the channel 16.

In the embodiment depicted here the pitch G of the screw flights 14 increases from an initial pitch value G1=500 mm by way of G2=550 mm to G3=600 mm, i.e. the smallest pitch value at the start of the conveying zone 18 along the channel can be 83% of the largest pitch value at the end of the conveying zone 18. The smallest pitch value G1 along the channel can also be at most between 20% and 85% of the largest pitch value G3 along the channel. The screw flights 14 can have the second pitch value G2=550 mm in the shank segments W2 to W3. The pitch G can therefore increase to G3 in the shank segments W3 to W4. This leads to a pressure decrease and transport volume increase along the channel 16 in the conveying direction 20 in the region of the shank segments W2, W3 and W4.

It is also possible, in an alternative embodiment not shown here, that the pitch decreases in stages from an initial pitch value G1=500 mm; the screw flights 14 can have the second pitch value G2=460 mm in the shank segment W2. It is also therefore possible, in an embodiment not shown here, that the pitch decreases from an initial pitch value G1=500 mm by way of G2=460 mm to G3=350 mm and then optionally further decreases to a value G4<350 mm; i.e. the smallest pitch value along the channel can also, at the end of the conveying zone 18, be 70%, or even less than 70%, of the largest pitch value. The smallest pitch value along the channel can also, at the end of the conveying zone 18, be at most between 20% and 80% of the largest pitch value along the channel at the start of the conveying zone 18.

In an alternative embodiment not shown here, on the one hand the pitch G therefore decreases especially in the shank segment W3, and on the other hand the shank diameter d increases. This leads to a pressure increase and transport volume decrease along the channel 16 in the conveying direction 20. In a first variant, this situation can be continued through the shank segments W4 and W5 (not shown) or accentuated in shank segments W4 and W5 by further increase of the shank diameter d (to d2 and then d3) and further reduction of the pitch G (to, for example, a value G4 and then G5—not shown).

The values of the mixing-element separation K2, K3, K4 and K5 in the working example shown in FIG. 3 have been adjusted to be appropriate for the pitch values G2, G3 of the pitch G of the screw flights 14 in a manner that gives negative correlation. While the values of the pin separations decrease from K2 to K5, the pitch values increase from G1 to G3. The direction of change of the mixing-element separation K is therefore the opposite to that of the change of the pitch G. This leads to a rather smaller pressure increase and transport volume decrease as a consequence of the increasing pitch G but to improved mixing and increased shear in conveying direction 20 toward the output zone 28 of the single-screw extruder 10 as a consequence of the decreasing pin separation K.

It is also possible, in a modification not shown here, to configure the change of the mixing-element separation K with positive correlation to the change of the pitch G. Using the reference signs of FIG. 3, the values of the mixing-element separation K2, K3, K4 and K5 in this modified working example would be adjusted to be appropriate for the pitch values G1, G2 and G3 of the pitch G of the screw flights 14 in a manner that gives positive correlation. While the values of the pin separations in the case of the modified embodiment would increase from K1 to K5 (not shown), the pitch values would also increase from G1 to G3 (shown) in a manner that gives positive correlation. This would lead to introduction of comparatively moderate pressure and shear forces as a consequence of the preference for avoidance of pressure increase and transport volume decrease, and on the other hand to mixing that is improved but exhibits no increase, i.e. to reduced shearing in conveying direction 20 toward the output zone 28 of the single-screw extruder 10.

Table 3 below collates the parameters of the working example of a laboratory-scale version and a production-scale version of a screw 12 by analogy with FIG. 3.

TABLE 3

| Property of screw or screw flights | Working example of screw of FIG. 3 (laboratory-scale version) | Working example of screw of FIG. 3 (production-scale version) |
|---|---|---|
| Channel width (W) | W | W |
| Flight land width (e) | 6 mm | 40 mm |
| Pitch (G = πD − e)tanΦ)) | 46 mm to 70 mm | 500 mm to 600 mm |
| External screw flight diameter (D) | 78 mm | 650 mm |
| Channel depth (H) | 43 mm | 310 mm |
| Shank diameter (d) (insofar as constant) | 35 mm | 340 mm |
| d/D | 0.45 | 0.52 |
| Distance between barrel wall and screw flight (δ) | δ | 5δ |
| Helix angle (Φ) | Φ1 to Φ2 | Φ1 to Φ2 |

FIG. 4 shows, in views (A1, A2), (B1, B2) and (C), preferred variants of pin arrangements 48 with pins for a mixing-element arrangement shown in FIG. 3; the pin arrangements are accordingly described as 48.A1, 48.A2, 48.B1, 48.B2 and 48.C. Each of the pin arrangements 48.A1 and 48.A2 has two pins 481, 482 arranged opposite on a diametral axis A. The pin arrangements 48.A1 and 48.A2 differ in the orientation of the diametral axis, the pins 481, 482 respectively being at a 12 o'clock position and 6 o'clock position (view A1) or the pins 481, 482 respectively being at a 3 o'clock position and 9 o'clock position (view A2).

In view A1 moreover by way of example the length L of a pin 481, 482 is in the region of about L=300 mm, and the distance I of a pin end from the surface of the shank 13 is in the region of about I=10 mm; the latter distance I can by way of example be in the range 10-25 mm. The length L of a pin 481, 482 can be in the range of about L=270 mm to 330 mm.

The pin length L protruding into the internal space 17 of the channel 16 is therefore preferably about 90% to 99% of the free channel depth H of the channel 16. The channel depth H is the distance between the wall of the channel 16 and the surface of the shank 13, and here is 310 mm. The diameter Q of a preferably round (but optionally possibly also oval or polyhedral) cross section of a pin is about Q=1-8 cm, preferably 2-6 cm, particularly preferably 4 cm. These pin arrangements 48.A1 and 48.A2 can also be combined for a mixing-element arrangement 49 along the conveying direction of the single-screw extruder 10, for example can alternate.

The pin arrangements 48.B1 and 48.B2 in each case have four pins 481, 482 and 483, 484 arranged in opposite pairs on a first and second diametral axis A1, A2. The pin arrangements 48.131 and 48.62 differ in the orientation of the diametral axis A1, A2, the pins 481, 482, 483, 484 respectively being at a 12 o'clock position and 6 o'clock position, and also 3 o'clock position and 9 o'clock position (view B1) or the pins 481, 482, 483, 484 respectively being at a 2 o'clock position and 8 o'clock position, and also 5 o'clock position and 11 o'clock position (view B2). These pin arrangements 48.131 and 48.62 can also be combined for a mixing-element arrangement 49 along the conveying direction of the single-screw extruder 10, for example can alternate. The dimensions of the pins of the pin arrangements 48.B1 and 48.B2 can be selected in the same way as for the pins of the pin arrangements 48.A1 and 48.A2.

The pin arrangement 48.C has eight pins 481, 482 and 483, 484, and also 485, 486 and 487, 488, arranged in opposite pairs; in practical terms, this is a superimposition of the pin arrangements 48.B1 and 48.B2. This pin arrangement 48.C can also be combined with the pin arrangements 48.B1 and 48.B2 and/or pin arrangements 48.A1 and 48.A2 for a mixing-element arrangement 49 along the conveying direction of the single-screw extruder 10.

It is also possible in principle to select other angular arrangements for the orientation of the pins in a pin arrangement 48 for a mixing-element arrangement 49.

Figure 5:
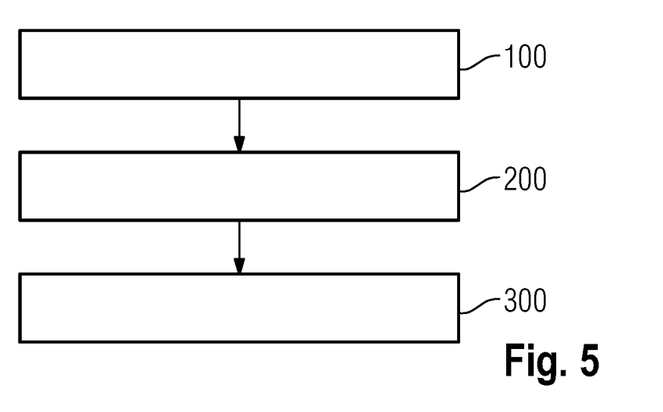
FIG. 5 a working example of a first preferred process for changing the morphology of a superabsorbent polymer gel (SAP polymer gel) with a single-screw extruder as in a preferred embodiment of FIG. 2 (with mixing elements that are not shown in that figure for reasons of clarity but which are present by way of example as in one of the variants of FIG. 4) or FIG. 3 (with the mixing elements that are shown in that figure and that are likewise provided as in one of the variants of FIG. 4)

FIG. 5 shows a first preferred working example of a process for changing the morphology of a superabsorbent polymer gel (SAP polymer gel) 24 with a single-screw extruder 10 of the preferred working examples of FIG. 2 (with mixing elements of a mixing-element arrangement 49 that are present but not shown in that figure) or FIG. 3 (with the mixing elements of a mixing-element arrangement 49 that are shown in that figure), i.e. in each case with mixing-element arrangements 49. The process has the following steps:

| | |
|---|---|
| 100 | introduction of the SAP polymer gel 24 from a polymerization process 38 into the single-screw extruder 10, |
| 200 | operation of the single-screw extruder 10 in order to change the morphology of the SAP polymer gel 24 and |
| 300 | discharge of the SAP polymer gel 44 with changed morphology from the single-screw extruder 10 to a drying process 46. |

The polymerization process of the step 100 produces what is known as a main polymer as basis for the SAP polymer gel 24 in accordance with the formulation of table 1. It is also possible to use other formulations.

Operation of the single-screw extruder 10 in step 200 uses the drive motor 40 to rotate the shank 13 of the screw 12, and conveys SAP polymer gel 24 from the input aperture 36 to the output aperture 30. The morphology of the SAP polymer gel 24 can be changed during conveying of the SAP polymer gel 24 along the conveying zone 18. The conveying zone 18 also serves as supply zone for the output zone 28, which serves as metering zone for the output aperture 30. The supply of SAP polymer gel 24 to the output zone 28, which is dependent inter alia on the parameters of the screw 12 and the rotational velocity thereof, provides a defined quantity of SAP polymer gel 24 in the output zone 28. A defined pressure can then be used to discharge said defined quantity via the output aperture 30. The output aperture 30 has shaping components which change the morphology of the SAP polymer gel 24. In the working example of the process in FIG. 5, the output aperture 30 comprises a perforated plate 32 and a downstream die 34. It is also possible that other components are arranged, alternatively or additionally, at the output aperture 30, an example being a matrix or other components that change the morphology of the SAP polymer gel 24.

The drying process 46 in step 300 in this working example of the process of FIG. 5 has the following steps:
  distribution of the SAP polymer gel 44 with changed morphology on metal drying sheets and heating of the SAP polymer gel 44 with changed morphology on the metal drying sheets in a convection oven.

Various quantities of SAP polymer gel 44 with changed morphology can be charged to the metal drying sheets; the charge level therefore depends on the area of the metal drying sheet and on the quantity of the SAP polymer gel 44 with changed morphology charged to the metal drying sheet. The drying temperature and drying time depend on the charge level. This working example uses a drying temperature of 175° C. for 70 minutes with a charge level of 0.91 g/cm². The metal drying sheets in this working example comprise a sieve tray with 250 μm mesh apertures, so that the liquid can also escape through the sieve tray. The sieve tray in this working example is composed of wires, the diameter of each wire being 130 μm.

Figure 6:
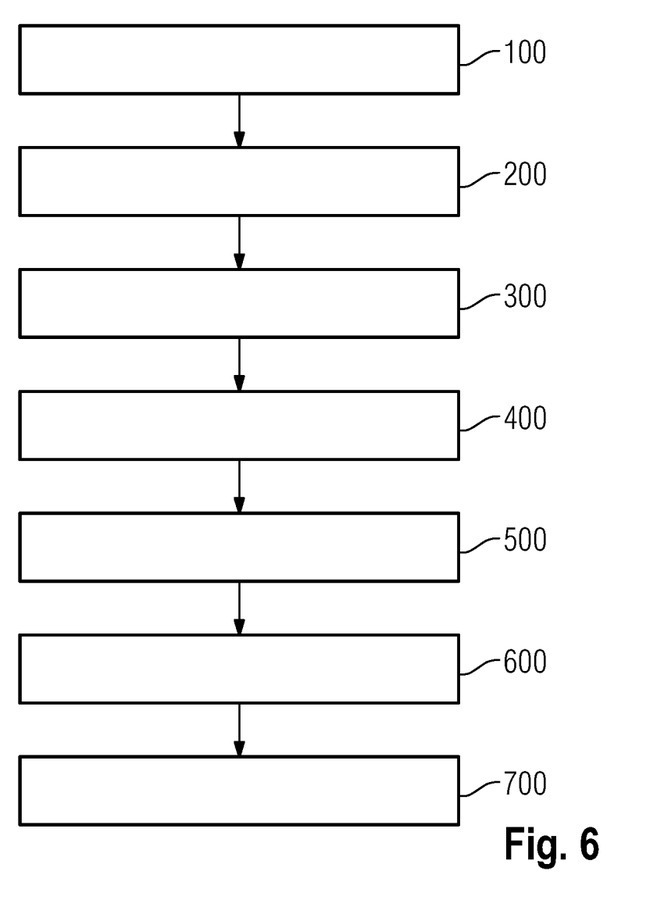
FIG. 6 another working example of a preferred process for changing a morphology of a superabsorbent polymer gel (SAP polymer gel) with a single-screw extruder as in a preferred embodiment of FIG. 2 (with mixing elements that are not shown in that figure for reasons of clarity but which are present by way of example as in one of the variants of FIG. 4) or FIG. 3 (with the mixing elements that are shown in that figure and that are likewise provided as in one of the variants of FIG. 4).

FIG. 6 shows a second preferred working example of a process for changing a morphology of a superabsorbent polymer gel (SAP polymer gel) 24, with a single-screw extruder 10 of the preferred working examples of FIG. 2 or FIG. 3, in each case with mixing-element arrangements 49. The process has the following steps:

| | |
|---|---|
| 100 | Introduction of the SAP polymer gel 24 from a polymerization process 38 into the single-screw extruder 10. |
| 200 | Operation of the single-screw extruder 10 in order to change the morphology of the SAP polymer gel 24. |
| 300 | Discharge of the SAP polymer gel 44 with changed morphology from the single-screw extruder 10 into a drying process 46. |
| 400 | Introduction of the dried SAP into a grinding process, in order to grind the SAP. |
| 500 | Introduction of the ground SAP into a sieving process or classification process, in order to sieve or classify the SAP. |
| 600 | Introduction of classified SAP particles into a mixing process, in order to mix the SAP particles. |
| 700 | Introduction of the SAP particle mixture into a surface-postcrosslinking process or surface crosslinking (SXL) process, in order to carry out surface-postcrosslinking on the surfaces of the SAP particles. |

The steps 100, 200 and 300 of the process are the same as the steps described in FIG. 5 of the working example of the process for changing the morphology of a superabsorbent polymer, specifically a polymer gel (SAP polymer gel) 24, with a single-screw extruder 10. The dried SAP is ground by a mill in the grinding process in step 400; SAP particles with various sizes can be produced. In the sieving process or classification process of the step 500, the ground SAP is sieved or classified in a manner that separates SAP particles with various sizes from one another. The mixing process of the step 600 mixes SAP particles of various sizes in accordance with a predetermined mixing ratio, in order to obtain desired properties of the SAP particle mixture. In this working example, an SAP particle mixture was produced with particle size distribution (psd) in accordance with table 4.

TABLE 4

| Sieve range | >710 μm | 710-600 μm | 600-500 μm | 500-300 μm | 300-200 μm | 200-150 μm | <150 μm | Total |
|---|---|---|---|---|---|---|---|---|
| Proportion (% by weight) | 0 | 10.6 | 27.9 | 42.7 | 13.8 | 5.0 | 0 | 100.0 |

In the surface-postcrosslinking process (SXL process) of step 700, a surface-crosslinking substance is applied to the surface of the SAP particles. The surface-crosslinking substance in this working example was produced in accordance with the formulation shown in table 5 below:

TABLE 5

| | | |
|---|---|---|
| Liquid fraction | 4.54% by weight baP | (isopropanol/water = 30.9/69.1) |
| Heonon/1,3-PG | 0.07/0.07% by weight baP | |
| 1,2-PG | 0.7% by weight baP | |
| Isopropanol | 0.99% by weight baP | |
| Span 20 | 40 ppm baP | |
| Aluminum lactate | 0.5% by weight baP | (in the form of 22% by weight of liquid solution Lohtragon AL 220) |
| Temperature | 185° C. | |

Heonon is 2-hydroxyethyl-2-oxazolidinone. It is also possible to use other formulations for production of the surface-crosslinking substance as alternative to the formulation in table 6. By way of example, alternative surface-crosslinking substances can comprise heonon, isopropanol, aluminum lactate and/or aluminum sulfate.

The SAP particles wetted with surface-crosslinking substance are heated at a temperature of 185° C. in a manner that brings about surface crosslinking on the respective SAP particles. The surface crosslinking allows the SAP particles to maintain their shape in the swollen state, i.e. when the SAP particles have absorbed liquid and take the form of polymer gel. In particular, the surface crosslinking can increase retention capability for absorbed liquid under pressure.

LIST OF REFERENCE SIGNS

10 Single-screw extruder
12 Screw
13 Shank
14 Screw flight(s)
16 Channel
17 Internal space of channel
18 Conveying zone
20 Conveying direction
22 Screw thread
24 SAP polymer gel
26 Input zone
28 Output zone
30 Output aperture
32 Perforated plate
34 Die
36 Input aperture
38 Polymerization process
40 Drive motor
42 Heating device
44 SAP polymer gel with changed morphology
46 Drying process
48 Pin arrangement
48.1, 48.2 Pins
481, 482, 483, 484 Pins
485, 486, 487, 488 Pins
49 Mixing-element arrangement
50 Cutout A Diametral axis of pins
G Pitch (G=π(D−e)tan φ)
G1, G2, G3, G4 Pitch value
d, Δd Shank diameter
d1, d2, d3 Shank diameter value
D External screw flight diameter
H Channel depth
L Pin length
I Distance between pin and surface of shank 13
Q Diameter of cross section of pin
K Mixing-element separation
K1, K2, K3, K4 Mixing-element separation value
W Channel width
W1, W2, W3, W4, W5, W6 Shank segment
e Flight land width
δ Distance between channel wall and screw flight
φ Helix angle

The invention claimed is:

1. A single-screw extruder (10) for changing a morphology of a superabsorbent polymer gel (SAP polymer gel) (24), having:
an input aperture (36) for the introduction of SAP polymer gel (24),
connected to the input aperture (36), a channel (16),
arranged in the channel (16), a screw (12) for conveying, and changing the morphology of, the SAP polymer gel (24), and
connected to the channel (16), an output aperture (30) for the discharge of the SAP polymer gel (44) with changed morphology,
where the screw (12) has a shank (13) and has screw flights (14) arranged on the shank (13) and is arranged and configured to convey the SAP polymer gel (24) from the input aperture (36) to the output aperture (30) by means of the screw flights (14),
where the channel (16) has an input zone (26) arranged at, or in the vicinity of, the input aperture (36), an output zone (28) arranged at, or in the vicinity of, the output aperture (30), and a conveying zone (18) extending along the channel (16) from the input zone (26) to the output zone (28),
wherein
the screw (12) has a pitch value of a pitch (G) of the screw flights (14) along the conveying zone (18) of the channel (16), and where the channel (16) has at least one mixing-element arrangement (49) with at least one mixing element which protrudes into the channel (16) of the single-screw extruder and which is configured for the mixing of the SAP polymer gel (24);
wherein the mixing-element arrangement (49) has a pin arrangement (48) comprising at least one pin (48.1, 48.2) extending into an internal space (17) of the channel (16), and has at least one cutout (50) along the screw flights (14), the at least one pin (48.1, 48.2) extending in particular into the at least one cutout (50) of the screw flights (14);
wherein the channel (16) has at least two pins (48) arranged along the channel (16) in the conveying direction (20) and separated from one another by a mixing-element separation (K), and there is a negative correlation between a value of the mixing-element separation (K1, K2, K3, K4) and a pitch value (G1, G2, G3) of the pitch (G) of the screw flights (14);
the negative correlation between the mixing-element separation (K) and the pitch (G) is such that a smaller value of the mixing-element separation (K1, K2, K3, K4, K5) is provided when a larger pitch value (G1, G2, G3) is provided; and
wherein the pitch values (G1, G2, G3, G4) change so as to increase along the conveying direction (20), and the change of the mixing-element separation values (K1, K2, K3, K4, K5) along the conveying direction (20) proceeds in an opposite manner with respect to the change of the pitch values (G1, G2, G3, G4) along the conveying direction (20).

2. The single-screw extruder (10) according to claim 1, where the screw (12) has a first pitch value (G1) of a pitch (G) of the screw flights (14) along the conveying zone (18) of the channel (16) and, following in conveying direction (20), has a second pitch value (G2) of the pitch (G) of the screw flights (14) along the conveying zone (18) of the channel (16).

3. The single-screw extruder (10) according to claim 2 wherein the second pitch value (G2) is larger than or equal to the first pitch value (G1).

4. The single-screw extruder (10) according to claim 2 wherein the second pitch value (G2) smaller than the first pitch value (G1).

5. The single-screw extruder (10) according to claim 1, where the screw (12) has, along the channel (16), at least three different pitch values (G1, G2, G3, G4) of the screw flights (14).

6. The single-screw extruder (10) according to claim 1, where the pitch (G) of the screw flights (14) increases along the conveying zone (18) of the channel (16), where the screw flights (14) have a smallest pitch value (G1) along the conveying zone (18) at a transition from the input zone (26) to the conveying zone (18) and a largest pitch value (G2) along the conveying zone (18) at a transition from the conveying zone (18) to the output zone (28).

7. The single-screw extruder (10) according to claim 1, wherein the screw flights (14) are rotated during operation, rotation of the shank (13) of the screw (12) therefore being possible without contact between the pin (48.1, 48.2) and the screw flights (14).

8. The single-screw extruder (10) according to claim 1, with at least one pitch value (G1, G2, G3, G4) of the screw flights (14) between 30 mm and 800 mm.

9. The single-screw extruder (10) according to claim 1, with a value of a flight land width (e) of the screw flights (14) between 4 mm and 80 mm.

10. The single-screw extruder (10) according to claim 1, where at least one value of a channel depth (H) between the shank (13) of the screw (12) and a wall of the channel (16) is between 25 mm and 500 mm.

11. The single-screw extruder (10) according to claim 1, with a value of an external screw flight diameter (D) between 60 mm and 1000 mm.

12. The single-screw extruder (10) according to claim 1, with at least one value of a shank diameter (d) between 25 mm and 500 mm.

13. The single-screw extruder (10) according to claim 1, with a ratio d/D of shank diameter (d) to external screw flight diameter (D) between 0.4 and 0.6.

14. The single-screw extruder (10) according to claim 1, where the pitch (G) increases along the conveying zone (18) from a pitch value (G1) of 500 mm in the vicinity of the input zone (26) to a pitch value (G4) of 600 mm in the vicinity of the output zone (28).

15. The single-screw extruder (10) according to claim 1, where the screw (12) has, along the channel (16), a smallest pitch value (G1) that is at most between 20% and 85% of a largest pitch value (G4) along the channel (16).

16. The single-screw extruder (10) according to claim 1, where the single-screw extruder (10) is configured to produce an SAP polymer gel (24) with a desired morphology that increases the water absorption of the SAP, and with throughput at least 23 metric tons per hour.

17. The single-screw extruder (10) according to claim 1, which has a drive motor (40) and/or a heating device (42),
 where the drive motor (40) is configured to rotate the shank (13) of the screw (12) at up to 150 revolutions per minute, and/or
 where the heating device (42) is configured to heat the channel (16) so that the temperature thereof is between 85° C. and 140° C., at least in the input zone (26), where during operation of the single-screw extruder (10) the temperature of the SAP polymer gel (24) in the channel (16) increases along the conveying direction (20) as far as an output zone (28), by a temperature in the range from 20° C. to 40° C., and moreover directly after the output aperture (30) the SAP polymer gel (24) the cooled SAP polymer gel (24) has a reduced temperature between 90° C. and 110° C.

18. A process for changing the morphology of a superabsorbent polymer gel (SAP polymer gel) (24) with a single-screw extruder (10) according to claim 1 comprising:
 introducing the SAP polymer gel (24) from a polymerization process (38) into the single-screw extruder (10),
 operating the single-screw extruder (10) in order to change the morphology of the SAP polymer gel (24), and
 disclosing the SAP polymer gel (44) with changed morphology from the single-screw extruder (10) to a drying process (46).

19. A single-screw extruder (10) according to claim 1 for use in changing a morphology of superabsorbent polymer gel (SAP polymer gel) (24).

* * * * *